US007546156B2

(12) United States Patent
Madden et al.

(10) Patent No.: US 7,546,156 B2
(45) Date of Patent: Jun. 9, 2009

(54) METHOD OF INDEXING BIOLOGICAL IMAGING DATA USING A THREE-DIMENSIONAL BODY REPRESENTATION

(75) Inventors: Brian C. Madden, Rochester, NY (US);
Craig C. Miller, Pittsford, NY (US);
Alice P. Pentland, Penfield, NY (US)

(73) Assignee: University of Rochester Medical Center, Rochester, NY (US)

( * ) Notice: Subject to any disclaimer, the term of this patent is extended or adjusted under 35 U.S.C. 154(b) by 458 days.

(21) Appl. No.: 10/840,932

(22) Filed: May 7, 2004

(65) Prior Publication Data

US 2005/0033142 A1 Feb. 10, 2005

Related U.S. Application Data

(60) Provisional application No. 60/469,617, filed on May 9, 2003.

(51) Int. Cl.
*A61B 5/05* (2006.01)
*G06F 17/00* (2006.01)
(52) U.S. Cl. .................. 600/476; 707/100; 600/407
(58) Field of Classification Search ................. 600/306, 600/407; 382/128; 707/2, 3, 6, 100
See application file for complete search history.

(56) References Cited

U.S. PATENT DOCUMENTS

| 5,561,754 | A | * | 10/1996 | Oliver et al. ............... 345/441 |
|---|---|---|---|---|
| 5,836,872 | A | | 11/1998 | Kenet et al. |
| 5,893,095 | A | | 4/1999 | Jain et al. |
| 5,911,139 | A | | 6/1999 | Jain et al. |
| 5,913,205 | A | | 6/1999 | Jain et al. |
| 5,915,250 | A | | 6/1999 | Jain et al. |
| 5,995,138 | A | | 11/1999 | Beer et al. |
| 6,032,120 | A | | 2/2000 | Rock et al. |
| 6,049,622 | A | | 4/2000 | Robb et al. |
| 6,243,095 | B1 | | 6/2001 | Shile et al. |
| 6,529,626 | B1 | * | 3/2003 | Watanabe et al. ............ 382/154 |

OTHER PUBLICATIONS

DermaGraphix Product, from http://www.canfieldscicom/special/bodymap.shtml, dated Jul. 30, 2004 (2 pages).
MoleMax II Product, from http://www.molemaxii.com/pages/intro/html, dated Jul. 30, 2004 (1 page).

(Continued)

*Primary Examiner*—Eric F Winakur
*Assistant Examiner*—Michael T Rozanski
(74) *Attorney, Agent, or Firm*—Townsend and Townsend and Crew LLP

(57) ABSTRACT

A system and method for managing imaging data related to a biological trait, including generating a three-dimensional representation of the external surface of the body a patient; obtaining the imaging data; associating the imaging data with a coordinate location of the three-dimensional representation, to generate an associated imaging data; and managing the associated imaging data using the surface representation. The association includes uniquely associating numerical values (e.g., Cartesian coordinates) to particular surface features. The three-dimensional model includes the ability to adjust the pose of the 3D models made from data taken at different times so that the coordinate systems closely correspond.

54 Claims, 4 Drawing Sheets

OTHER PUBLICATIONS

Aguiar, Pedro M.Q. et al.; "Three-Dimensional Modeling from Two-Dimensional Video"; 2001, *IEEE Transactions on Image Processing*, vol. 10, No. 10, pp. 1541-1551.

Allen, Brett et al.; "Articulated Body Deformation from Range Scan Data"; 2002, *Association for Computing Machinery, Inc.*, pp. 612-619.

Allen, Brett et al.; "The space of human body shapes: reconstruction and parameterization from range scans"; 2003, *ACM*, pp. 587-594.

Alliez, Pierre et al.; "Progressive Compression for Lossless Transmission of Triangle Meshes"; University of Southern California, 9 pages.

Benaron, David A.; "The Future of Cancer Imaging"; 2002, *Cancer and Metastasis Reviews*, vol. 21, pp. 45-78.

Bock, Mitchum et al.; "Data extraction from dense 3-D surface models"; University of Glasgow, pp. 1-6.

Chetverikov, D. et al.; "The Trimmed Iterative Closest Point Algorithm"; Computer and Automation Institute, 4 pages.

Halpern, Allan C. et al.; "Standardized positioning of patients (poses) for whole body cutaneous photography"; 2003, *J. Am. Acad. Dermatol.*, pp. 593-598.

Johnson, Andrew Edie et al.; "Surface Registration by Matching Oriented Points"; 1997, *International Conference on Recent Advances in 3-D Digital Imaging and Modeling*, 8 pages.

Ju, Xiangyang et al.; "Individualising Human Animation Models"; *3D MATIC Laboratory*, University of Glasgow, 5 pages.

Lee, Won-Sook et al.; "Virtual Body Morphing"; 2001, *IEEE*, pp. 158-166.

Marghoob, Ashfaq A. et al.; "Instruments and new technologies for the in vivo diagnosis of melanoma"; 2003, *Journal of the American Academy of Dermatology Editorial Office*, pp. 777-800.

McGregor, Bruce; "Automatic Registration of Images of Pigmented Skin Lesions"; 1998, *Pattern Recognition*, vol. 31, No. 6, pp. 805-817.

Natarajan, Vijay et al.; "Simplification of Three-dimensional Density Maps"; 1999, Duke University, pp. 1-11.

Oliveira, Joao Fradinho et al.; "Animating Scanned Human Models"; Department of Computer Science, 2003, *Journal of WSCG*, vol. 11, No. 1, 8 pages.

Pollefeys, Marc et al.; "Video-To-3D"; University of North Carolina, 6 pages.

Seo, Hyewon et al.; "Synthesizing Animatable Body Models with Parameterized Shape Modifications"; 2003, *Eurographics/SIGGRAPH Symposium on Computer Animation*, pp. 120-125.

Smith, Jason McC. et al.; An Extensible Object Tracking Architecture for Hyperlinking in Real-time and Stored Video Streams; 2002, University of North Carolina at Chapel Hill, *Technical Report TR02-017*, pp. 1-11.

Wang, Steven Q. et al.; "Detection of melanomas in patients followed up with total cutaneous examinations, total cutaneous photography, and dermoscopy"; 2004, *J. Am. Acad. Dermatol.*, pp. 15-20.

\* cited by examiner

METHOD OF INDEXING BIOLOGICAL IMAGING DATA USING A THREE-DIMENSIONAL BODY REPRESENTATION

CROSS-REFERENCES TO RELATED APPLICATIONS

This application claims priority to U.S. Provisional Patent Application No. 60/469,617, filed May 9, 2003, the disclosure of which is hereby incorporated by reference herein in its entirety for all purposes.

BACKGROUND OF THE INVENTION

The present invention relates to methods and systems for the managing of imaging data related to a biological trait.

For various reasons, medical information on the state of a patient is often non-uniformly known. Accessing a given piece of imaging data, or comparing imaging data for a given location that has been collected over time, can be a rather difficult organizational task given that the human body does not come with a quantitative coordinate system.

At present, clinical body maps consist of several macro images of lesions taken using slide films. While the demands of imaging quality call for the use of slides and slide film as a preferred medium for clinical imaging, complete coverage of the approximately 2 square meters of skin surface found on the average body would require some 200 images, each covering approximately 100 square centimeters. However, not all of these images are diagnostically relevant. An appreciable reduction in the total volume of data has been accomplished by obtaining high resolution images of the lesions alone. On the other hand, omitting coverage of some regions runs the risk of not documenting potential problems that are not immediately manifested. Total coverage with a resolution sufficient to identify differences of non-involved skin provides an historical record that may be subsequently retrieved to create a more accurate timeline of events later determined to be of interest. However, in order to track a patient's condition, individual slides of small regions must be uniquely labeled and manually compared to track changes across patient visits to the clinician. However, for the image-based diagnoses and comparisons to be clinically effective, a diagnostic system needs to be able to uniquely and clearly identify a lesion that appears disembodied and without context, especially when viewed through a small aperture. Furthermore, such a system needs to be able to direct the clinician to the appropriate site on a subsequent visit and guide the clinician to obtain a subsequent image using similar or identical photographic settings, such as lighting, filtering and so on. Such a system remains elusive.

Additionally, while computer technology and digital imaging has enabled products to characterize individual lesions and compare pairs of images taken at different time; some even correcting spatial distortions brought on by differences in acquisition conditions; a coordinate system is still lacking. A problem is that the shape of the human body is complex and articulated with a deformable surface that is without a clear frame of reference or even helpful landmarks over large regions. Besides lacking a coordinate system, another problem with digital imaging is that most common digital images lack the requisite resolution to support diagnostic decisions, and digital images that have the requisite resolution tend to generate electronic files that are rather large in size, and thus unruly to manage. Another problem that needs to be addressed is the effect of the pose and its interaction with the available lighting. Furthermore, the problems of pose and lighting and camera positions are further exaggerated by the effects of gravity on patient's skin.

There is therefore a need for a system that allows for an effective management of medical imaging data in light of the aforementioned difficulties.

BRIEF SUMMARY OF THE INVENTION

The present invention provides a system and a method for managing imaging data related to a biological trait, including generating a three-dimensional representation of the external surface of the body a patient; obtaining the imaging data; associating the imaging data with a coordinate location of the three-dimensional representation, to generate an associated imaging data; and managing the associated imaging data using the surface representation. The association includes uniquely associating numerical values (e.g., Cartesian coordinates) to particular surface features. The three-dimensional model includes the ability to adjust the pose of the 3D models made from data taken at different times so that the coordinate systems closely correspond.

In one aspect, the present invention provides a method of assigning a body-surface coordinate system to an imaging data related to a dermatological characteristics. The method includes generating a three-dimensional representation of the external surface of the body a patient; rigging the three-dimensional representation to generate an articulated representation; normalizing the three-dimensional representation for overall geometric reference dimensions; normalizing the three-dimensional representation for cardinal reference points; texture mapping the three-dimensional representation using low resolution 2D surface images; texture mapping portions of the three-dimensional representation with high resolution dermatological images; assigning the coordinate dimensions of the underlying mesh of the three-dimensional representation to the high resolution dermatological images; interpolating 3D coordinates of the dermatological characteristics of the high resolution dermatological images from the nearest mesh vertices; and assigning the interpolated coordinates to the dermatological characteristics.

For a further understanding of the nature and advantages of the invention, reference should be made to the following description taken in conjunction with the accompanying drawings.

DETAILED DESCRIPTION OF THE INVENTION

Figure 1:
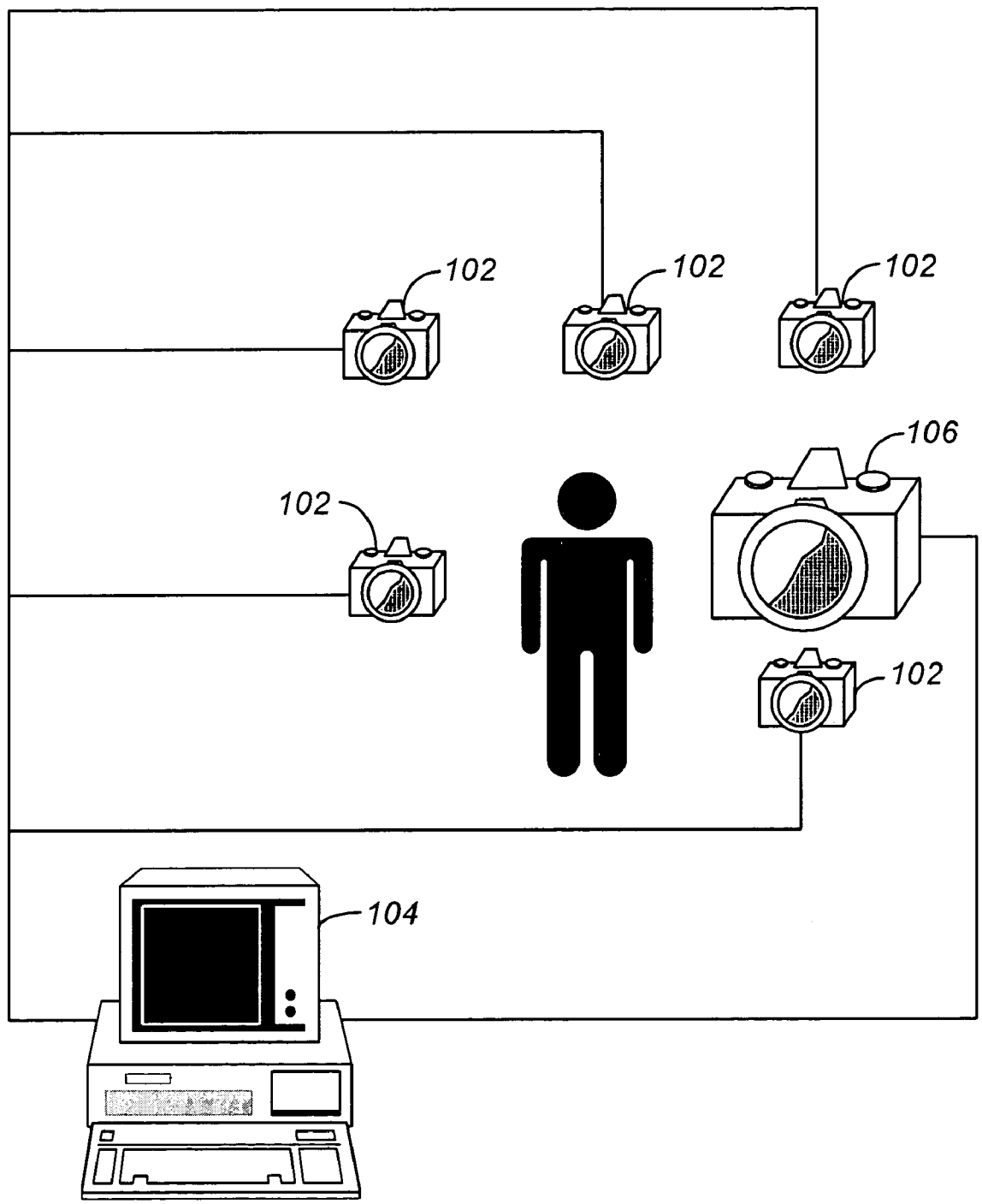
FIG. 1 is a diagram of a system for the management of medical imaging data in accordance with one embodiment of the present invention.

Embodiments of the present invention provide an information structure that is used to organize medical imaging data. In particular, embodiments of the invention use a three-dimensional representation of the body of a human which has been adapted to or obtained directly from an individual patient as a frame of reference for medical imaging data. A three-dimensional representation of the body surface of a patient, being a mathematical representation, has an intrinsic coordinate system that very intuitively lends itself for use as an index for medical imaging data.

The embodiments of the present invention combine the advances in computer hardware, software and sensor technology in the areas of three-dimensional model building to provide a three-dimensional representation of the surface of the body of a patient to organize medical data obtained from the patient. The use of a three-dimensional representation enables medical data, including medical imaging data to be linked to a volumetric-based representation. The medical data that is linked with the three-dimensional representation may include a single discrete data point, a series of such data points, an image, or an image hierarchy that is integrated with a discretized three-dimensional representation having a mesh or a grid. The mesh or the gird may be a fixed resolution grid or preferably a variable resolution mesh. Once the medical data has been associated or linked with the three-dimensional representation, it is readily retrievable and identifiable.

Certain embodiments of the present invention are directed to the use of the three-dimensional representation as an indexing system for dermatological image data management. As used herein, in connection with dermatological and other imaging data, data management includes the tagging, labeling, localization, cataloging, accessing, retrieving, monitoring, and comparing of image data. As it relates to dermatologic data, the information structure (i.e., using a three-dimensional mesh as an indexing system for dermatological image data management) of the present invention has many applications, including skin mole management (e.g., mapping and monitoring); monitoring the effectiveness of a drug, cosmetic treatment or plastic surgery as applied to tissue, skin, skin lesions or skin burns; and the identification of individuals (e.g., bioinformatics or forensic applications). As is relates to the identification of individuals, it is noted that the cutaneous vasculature pattern differs significantly across individuals but not significantly within an individual over time.

An example of the use of the embodiments of the present invention in a dermatological setting includes the linking of a high resolution dermatological image with a unique location or area on the three-dimensional representation, preferably in an electronic manner using a computer-based system. Once the high resolution image is linked in this manner, its cataloguing and later retrieval are easily accomplished by simply pointing a pointing device, such as a computer mouse, on a particular location on the three-dimensional representation that is presented on a computer display, to retrieve the particular high-resolution image. Besides the location data of the high-resolution image (i.e. with respect to a location on the three-dimensional representation) other information related to the high-resolution image may also be stored along with the high-resolution image. Such additional information includes information related to the image capture, such as the camera position, camera's exposure settings, lighting levels, use of and type filter(s) used, and so on. Such additional information is used by a clinician for a subsequent comparison and diagnosis. For example, the growth of a particular skin lesion can be easily tracked in the manner described below by comparing two captured images of a given lesion. In accordance with embodiments of the present invention, there is no need to have identically captured images in order to allow a comparison. One of the benefits of the indexing mesh is that images taken with different poses of the camera relative to a lesion can be registered relative to the model and thereby eliminate distortions consequent to the particulars of the capturing of the images. On a first visit, a high resolution image is obtained and it is associated with a particular location on the three-dimensional representation that corresponds with the actual location of the image on the patient's body. Clinically relevant information, including the additional information described above, is also stored along with the high-resolution image. Then on a later visit, as a part of the diagnosis, the three-dimensional representation is viewed on a computer display, and the clinician selects a location on the representation. The selection will cause the previously obtained high-resolution image to be brought up for viewing and for providing the various other information such as, camera set up, etc. to the clinician. Using this information, the clinician is able to then take another high-resolution image using an identical setup as that used when the previous image was taken. In this manner, the clinician will have two images taken from the same location that use the same image capture setup to allow for an effective comparison of the changes in the patient's condition as it relates to the particular unique location.

In addition to the example described above, the indexing system of the present invention enables the monitoring of several to hundreds of unusual moles (e.g., dysplastic nevi) over time. The monitoring includes the comparison of the moles over time, which is usually achieved by comparing older images with newer ones to assess mole growth, new mole development and such. The proper locational indexing of the images of the patient's skin are crucial in the assessment of mole growth. Like the example described above, embodiments of the present invention link a particular image with a unique location of the patient's body, thus enabling the taking and comparing of a subsequent image.

A system 100 including the imaging equipment that may be used to practice the embodiments of the present invention is described below in conjunction with FIG. 1. Such a system includes digital imaging equipment 102 that is used to create a complete volumetric representation of the body of an individual subject. The system also allows for the efficient capture of high resolution images of the subject. Such a system may include one or more cameras 102. For example, an array of several (e.g., 27) digital cameras may be used where the cameras are triggered (e.g., synchronously) and are mounted on supports with illumination, filtering and a uniform background. As an alternative to capturing multiple images through the simultaneous triggering of multiple cameras, a patient may be positioned with some aid in maintaining position (e.g., in a door frame or with some other mechanical support) and then a smaller subset of cameras are used which could be repositioned to provide the needed coverage in terms of pixels per millimeter on the skin, or even to use a single camera to take all the required images sequentially. Software utilities running on a computer system 104 that is linked with the cameras are used to calibrate the cameras to obtain a complete set of images to generate a volumetric representation of the body of the subject. Additional software utilities are used to combine the multiple two-dimensional views into a three-dimensional representation including a surface mesh or gird. In addition to the camera array that is used to create a three-dimensional representation of the body of the subject, an additional higher resolution camera 106 (e.g., 5 mega pixel or higher) capable of producing macro images of lesions is also outfitted with supports, illumination and filtering. The combination of the high and regular resolution cameras and images is advantages for several reasons. One reason is that while high resolution images are necessary for diagnostic purposes, they tend to be larger in size and thus may be more burdensome to store and manage. On the other hand, lower resolution images, which tend to be smaller in size and thus are less burdensome to manage, are more than adequate to generate a three-dimensional representation of the body of the patient. The resolution of images required to define a surface whose spatial locus defines the index can be much lower than the resolution that might be required to subserve the making of an accurate diagnosis. The surface must be sufficiently true to the patient's body so that the subsequent mapping of data to that surface will not be confused with other data residing proximally to the locus of interest and also that representations taken at a later time are unambiguously congruent. There is an entire hierarchy of image resolution available from a variety of sensors, ranging from high to low resolutions. In this manner no relevant information is ignored. The entire hierarchy is used to form both the index surface and the diagnostic image. In this way, the index surface can increase spatial accuracy just where there are lesions of interest. The hierarchy of image data also affords representation of diseases across considerable scale. For example, the pattern of eruptions across the entire back of a patient is often as relevant as the detailed character of the individual eruptions. While both high and low resolution cameras may be used within the same system, it may more commonly be the case that high resolution (e.g., >5 megapixels) cameras alone are used and it is only the field of view (the amount of body surface covered) that is varied by moving closer or changing the focal length to obtain the desired image resolution. For example, 5 megapixels could be used to capture a 2 cm by 2 cm area for diagnosis, while the same pixels could be used to capture a 20 cm by 20 cm region for location and context. In order to help define what is meant by a high resolution image of the surface of the skin, it is noted that at present for dermatological diagnoses, Kodachrome film is the film of choice. The digital equivalent of such a film is approximately 70-72 pixels/mm. So an image having a resolution on the order of 70 pixels/mm or higher is considered high resolution image. Such high resolution images are typically used to obtain very fine detail in a skin mole or to image melanomas. On the other hand, the diagnoses and treatment of skin features such as scratches, and those caused by poison ivy or poison oak which involve the study of a pattern over a relatively large area, typically involve the using low resolution images.

In one embodiment, with sufficiently high resolution images, an accurate representation of the location of individual hair shafts emerging from their follicles is captured. The point of emergence may serve as a reference point for correspondence across images. Correspondence of the pattern of the array of hair shaft base locations is used to create a 3D mesh over the vast majority of the body's surface that is hirsute skin. This capability will be effective in most skin regions even though they may be featureless, devoid of landmarks or lesions. The small, overlapping regions are then stitched together as required. The 3D numeric index of the surface will accommodate the enhanced detail that can be generated by superresolution algorithms either from overlapping digital still images or from video streams.

Furthermore, in one embodiment, an articulation framework is installed into a 3D model (a rigging) to use it to alter the shape of the model. In this way, two data sets taken at different times can be made sufficiently congruent. Alternately, if the pose of sections of the model are sufficiently congruent to begin with (such as with a fairly rigid part as the shin or skull), the registration and matching may be done piecewise, in segments.

Using the system, appropriate camera and filter parameters including polarizations are used to acquire images of sufficient quality to allow a diagnostic comparison over time. The use of polarizers reduce the masking effect of the illumination on the skin (the specular reflectance) and thereby provide a better representation of the intrinsic reflectance of the skin itself.

The volumetric representation of the body of the subject then serves as a platform to integrate multiple overlapping lower resolution images onto a single higher resolution representations. This integration may be achieved with a series of still images or from a video of the skin surface.

The software utilities may use any one of several representational transforms to generate the three-dimensional representation from the series of 2D images. Using these transforms the images of the skin are remapped to a coordinate system with the body's anatomical landmarks anchored to canonical locations. Anatomical landmarks of the body include, for example, the submandibular area; the supraclavicular space; the sternal notch; the sternum; the clavicle; the armpit or the axilla, down to the thigh or the medial aspect and lower and so on. In addition to the software utilities described above, other utilities may be provided to make multiple three-dimensional images congruent. One such technique that may be adapted for this purpose involves the use of an animation package such as one provided by Maya (e.g., Alias) to provide the articulation tools to adjust multiple three-dimensional models obtained at different times in order to make them congruent. Quantitative changes in local regions of the patient's form may occur between visits but they are not likely to be qualitative and can be accommodated by local adjustments in the models. In addition, the landmark and lesion registration algorithms are made robust to perturbations in the position of individual points, as they are to the addition or deletion of points.

In operation, the three-dimensional representation may either be generated by using a series of 2D images obtained for each subject, or alternately, a catalog of different body types may be created and adapted to each individual subject. For the adoption, a few (e.g., 2) profile images (e.g., front, back and side) may be used to locally scale the three-dimensional representation that includes a mesh or the grid.

Since the need to capture a mosaic of 2D images of sufficient resolution both to create the mesh and to identify and to characterize, for example, a lesion can still be onerous, the use of a video camera instead of a still camera can be advantageous. A video camera may be used to capture in a continuous video stream the entire surface of the body of the patient. The captured images may then be processed to create a low resolution three-dimensional representation including a mesh that may be used as an indexing structure for the high resolution diagnostic type images. As it relates to the use of a video camera to capture a series of still images, with sufficient lighting, progressive scan camcorders may be used to capture video with short shutter durations and thereby avoid artifacts due to interlacing and to motion blur. These high quality video streams facilitate the collection of the data required to create a three-dimensional model.

An aspect of the management of the imaging data of the present invention is directed to the determination and the recording of the pose or the positional information associated with each captured image. The similarity of the subject's pose is related to aspects that are relevant to obtaining congruence of models and thereby establishing the correspondence of lesions. One way of obtaining the positional information involves the use of GPS technology using multiple GPS units to capture the relevant pose parameters (i.e., position and orientation). Alternately, by imaging the acquisition process itself, the position of the camera relative to the patient at the time each image was obtained is determinable. Local position systems that are available afford a high degree of accuracy within a given clinical setting. The local position system in conjunction with the intrinsic camera parameters enables the projection of the high-resolution images onto the three-dimensional representation that includes a positional mesh that represents the skin surface of the patient. The positional information is necessary to later map the 2D images onto a three-dimensional representation. As used herein, local positioning systems (such as an articulated mechanical arm (e.g., from Faro technologies Inc. or electronically with a room-sized GPS system) provide the location (x, y, z) and orientation (pitch, roll, yaw) of the camera (i.e., the extrinsic camera parameters) in a coordinate system defined locally (referenced to some point and orientation within the room). Also required for reconstruction of a three-dimensional model, are the intrinsic parameters of the camera (focal length, location of the nodal point, the location of the sensor relative to the optical axis, etc.). In one embodiment, the intrinsic parameters of the camera are be obtained by capturing multiple images of a calibration grid with varying camera pose.

Examples of image processing products that may be adapted to calibrate the cameras in the camera array and to construct a three-dimensional model including a mesh from a collection of still images include the suite of products available from Realviz® (e.g., ImageModeler®) and those from Eos System, Inc. (e.g., Photomodeler). In addition to these commercially available products that may be adapted for the purposes of practicing the embodiments of the present invention, other photogrammetry-based techniques are also equally viable as approaches to use to calibrate the camera array and construct a three-dimensional model including a mesh from a collection of still 2D images.

The indexing system in accordance with embodiments of the present invention, and its ability to link images with unique locations of the patient's body also allows for the determination of the efficacy of a particular treatment in clinical drug trials. In such drug trials, it is usually required to assess the changes in the severity and area of coverage of skin lesions (e.g., psoriasis, lupus, Cutaneous T Cell Lymphoma or CTCL). The embodiments of the present invention, by enabling an effective cataloging system enable such assessments.

Additionally, the embodiments of the present invention, and their ability to link images with unique locations of the patient's body also enable an accurate estimate of areas impacted for the effective treatment of burn victims.

In addition, the embodiments of the present invention, and their ability to link images with unique locations of the patient's body also allow for the determination of the effectiveness of cosmetic treatments. Relevant areas of a patient's skin that are planned to undergo cosmetic treatment can be catalogued and visually documented by indexing relevant images to the three-dimensional representation of the patient. For example, plastic surgeons may use embodiments of the present invention to precisely document the condition and appearance of a patient's skin both prior and subsequent to procedures. In addition to plastic surgery, there is a wide range of dermatological surgeries where tissue loss occurs in cosmetically sensitive areas where visualization and indexing in accordance with embodiments of the present invention would be beneficial.

In addition, the embodiments of the present invention, and their ability to link images with unique locations of the patient's body also allow for the identification of subjects, such as in biometrics applications. On example of such an identification is the identification of persons or body parts often required under circumstances, such as during wartime or natural catastrophes, where resources are limited. Furthermore, forensic work or criminal investigations often require detailed localizations of marks and injuries on a body. Embodiments of the present invention by associating an image of a portion of skin with a unique location of the body of a subject, enable this localization and identification.

When using the indexing system of the present invention for biometric or identification purposes, the surface map of a subject may be adapted to include the follicular pattern or the follicular pattern in conjunction with an indexed set of skin markings (nevi, vascularities) to uniquely identify an individual. A three-dimensional model that allows a more thorough mapping over larger regions of the skin or the entire body not only enables various medical applications, but it also offers additional dimensionality to the available properties that establish an individual's unique signature for identification purposes.

The embodiments of the indexing system and methods of the present invention are not limited to the indexing of the surface of the skin. Various non-invasive techniques that allow the capture of information about subsurface skin structures can also benefit from the indexing system as is taught by the embodiments of the present invention. For such applications, rather than using a global Cartesian volumetric representation (e.g., Visible Human Male), the subsurface information is itself referenced to the accurate three-dimensional representation including the mesh and its corresponding positional index. The use of surface positions or landmarks are advantageous over a solid volumetric representation in locating or returning to a subsurface structure with better accuracy that is available in a system that depends on a global Cartesian positioning metric. The system is advantageous because in a solid volumetric representation system that depends on a global Cartesian positioning metric, because of the volume it represents, the accuracy of the positioning tends to be rather coarse, since much of the resolution is wasted. The resolution is wasted, since in medicine it is not often that a structure in the toe must be accurately located relative to ear, rather, it is the local relative positioning that is important. The approach of the embodiments of the present invention are advantageous because the ability to accurately and repeatedly locate a cluster of tissue structures by referencing the surface mesh is based on an indexing system that precisely represents the portion of the body that is most accessible, namely the external skin structure. By contrast, solid three-dimensional representations that depend on scan slices have boundaries that are relatively imprecise. Therefore, the meshes constructed by stitching together these slice boundaries are consequently also imprecise.

Other imaging data related to a biological trait that may also be indexed using the three-dimensional surface representation of the present invention include the representations of all epithelial surfaces accessible non-invasively through the bodily orifices, such as the colon, or oral cavity. Other such epithelial surfaces include the gastrointestinal surface, vaginal and reproductive tract surfaces, the sinus cavity areas, the surfaces of the eyes (e.g., eye ground findings), and so on. Technologies such as the camera pill or an endoscope can also benefit by having a spatial index of the gastrointestinal surface to both locate lesions for future observation as well as to assist in locating landmarks that assist in stitching together multiple passes for a more complete coverage of the surface with a camera, especially since cameras such as those in an endoscope, do not have a spherical field of view. In addition to the camera pill and endoscopes, the colposcope used in the cervix can also benefit by having an indexing system in accordance with embodiments of the present invention.

In addition, the embodiments of the present invention may also be used to index other parameters, such as a thermal map of a patient. A three-dimensional representation of the thermal measurements of a patient is able to more accurately illustrate vascular and other anomalies associated with various disease processes.

Figure 2:
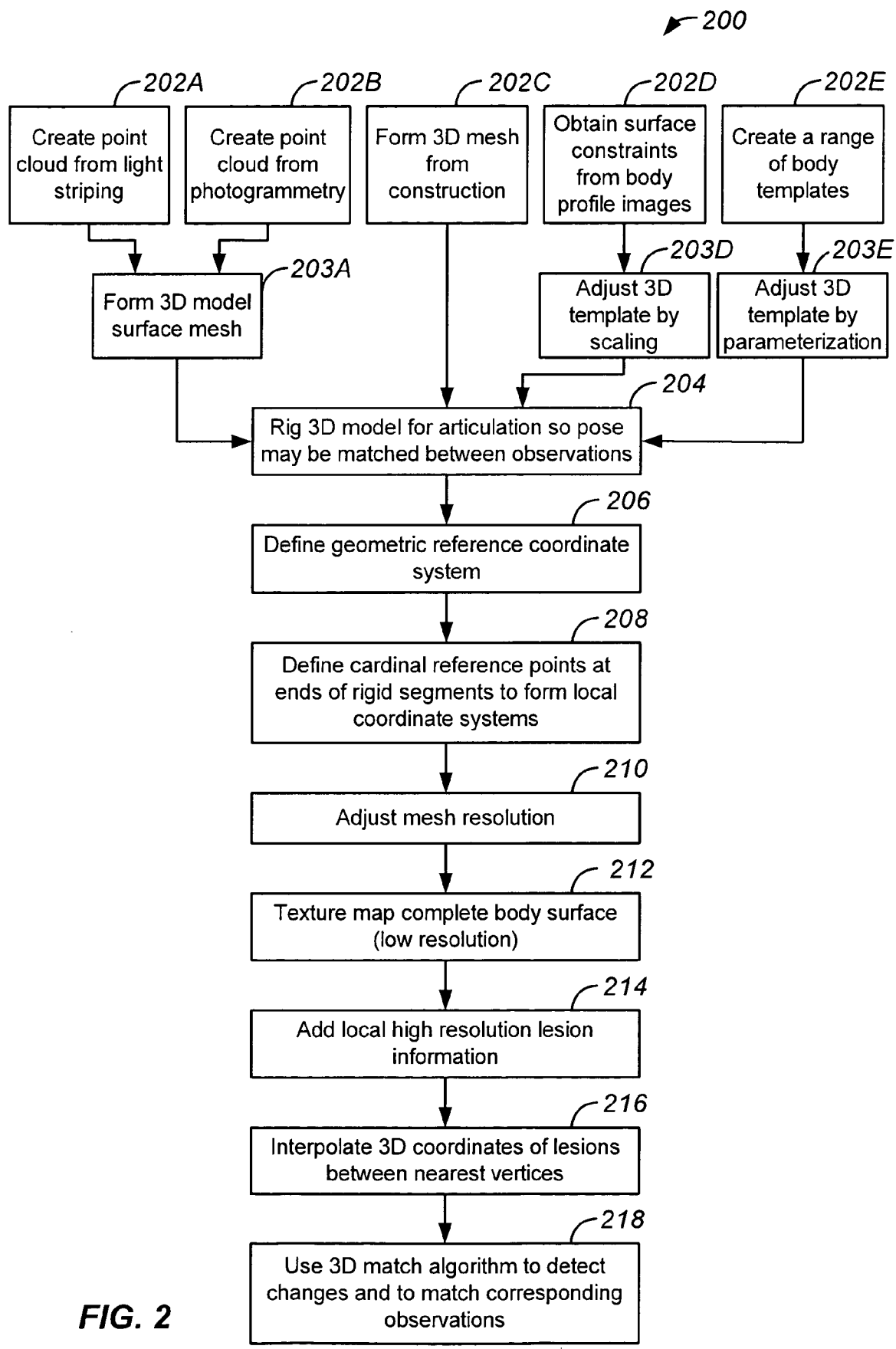
FIG. 2 is an exemplary flowchart of a method of managing medical imaging data in accordance with one embodiment of the present invention.

FIG. 2 is an exemplary flowchart 200 of a method of managing medical imaging data in accordance with one embodiment of the present invention. The flowchart describes, for example, that in one embodiment, the imaging data is used twice, once to generate a 3D surface representation of the body of the patient and again to associate a high-resolution image with the 3D surface representation. The flowchart describes the low resolution texture mapping of the 3D model and the insertion of the high resolution (diagnostic) lesion image information. The local high resolution information may either be superimposed by texture mapping or may be accessed by inserting a hyperlink at the indexed point. This hyperlink can open a new image window as well as access any other relevant documentation (clinical notes, other clinical imaging modalities such as epiluminescent microscopy).

As shown in FIG. 2, there are several methods of obtaining 3D models of the human body. Five of these methods are shown in the flowchart (202A-E). For example, block 202A represents various devices that use a combination of projected light and triangulation to locate 3D points on the skin (e.g., Minolta Vivid 900, Cyberware WB4). For example, block 202B represents the creation of a point cloud created using feature correspondences in multiple 2D images using photogrammetry software (e.g., EOS PhotoModeler, Realviz ImageModeler). Software (block 203A) is then used to fit the point cloud with a triangular mesh (e.g., Raindrop Geo-Magic). Alternatively, as shown in block 202C, the 3D mesh may be synthesized directly using modeling software (Alias Maya). Alternately, a 3D model of a patient may be obtained by using profile images of the patient to scale an existing template (blocks 202D and 203D). Parameterized models may also be created that allow direct adjustment of the shape of the volume (blocks 202E and 203E). In addition to the five methods of creating a 3D model, any combination of the methods may be useful. In particular, direct construction may be used to good effect in fine tuning details in the scanning-based methods.

Having generated a 3D surface representation, the 3D model is rigged (block 204) so that it may be articulated (Alias Maya). Multiple observations may then be brought into congruence through manipulation of the model's joints. Once brought into canonical alignment, a geometrically-based coordinate system is defined to provide a reference numbering system (block 206). Local anatomical features provide externally observable local references to rigid segments. The geometric reference and the local coordinate system (block 208) allow for the normalization of the 3D representation from one visit to the next, and hence enables the tracking and comparison of surface features on a normalized 3D representation. The geometric reference coordinate system is used to dimension the physical (e.g., height, width, origin) parameters of the 3D surface representation. For example, the apex of the head may be used as the origin and the tip of the big toe may be used as the end point for height determination. The setting up of a coordinate system involves: (1) making cardinal points that delimit rigid components and minimize the effects of articulation by positioning the patient in a standard pose across observations; (2) using a standard pose across observations and using an objective metric such as normalizing subsequent observation dimensions to those in the initial data set (e.g., select as an origin the front/back left/right centroid of the highest (or lowest) point). The coordinate systems (blocks 206 and 208) enable the setting of geometric and cardinal reference points to bring the 3D surface representation into registration using the articulation enabled by rigging the 3D model.

The surface mesh then may be adjusted (block 210) to balance the cost of the representation and the requirement for accuracy and discrimination. Next, high resolution images are registered with the low resolution images that are texture-mapped (block 212) over the mesh (block 214). Features in the high resolution image or the entire image are assigned 3D coordinates by interpolating from the nearest vertices (block 216). In one aspect, triangulation is used to locate points in 3D space. Multiple correspondences provide enough information to establish the relation between two images. Knowing the camera relations (pose) and the feature correspondences enable the generation of a mesh (e.g., usually and approximation surface fit to a cloud of points). The pixel values are then projected onto that surface (usually composed either of polygons connecting the 3D points or a NURBS surface fit to those points). Since these surfaces have a mathematical specification, this enables the interpolation between established features to obtain numerical values for nearby features. The combination of the proximal alignment of the multiple datasets and the possible redundancy of many corresponding skin markings, anatomical landmarks, and lesions of interest allow both matching and missing data to be identified with a high probability (block 218).

Figure 3A:
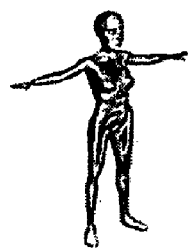
FIGS. 3A-E are exemplary images representing outputs of the method of FIG. 2.
Figure 3B:
Figure 3C:
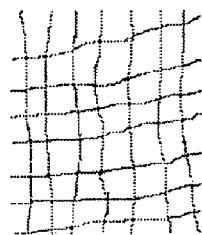
Figure 3D:
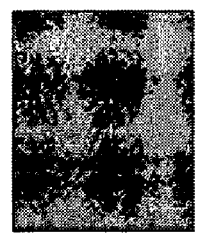
Figure 3E:
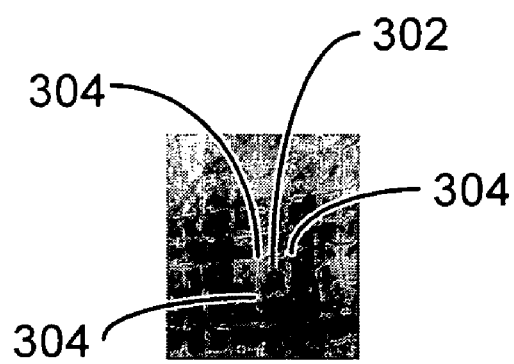

FIGS. 3A-E are exemplary images representing outputs of the method of FIG. 2, and which demonstrate the 3D spatial indexing of a lesion by interpolating between the vertices of a mesh. FIGS. 3A-E provide images representing the basic flow of 3D indexing a surface feature. As shown in FIG. 3A, the 3D body representation is created using one of the five (or other) methods described above. If the 3D body model doesn't provide sufficient resolution to index the features of interest, a wireframe model of a local region (e.g., the head) can be linked as shown in FIG. 3B. The mesh at this higher resolution provides the required resolution and a portion of the mesh is shown at greater magnification (FIG. 3C) along with the corresponding image pixels of the skin reflectance (FIG. 3D). When the corresponding pixels are texture mapped onto the 3D surface, the location of the mesh relative to the surface features may be observed (FIG. 3E). The interpolation of the 3D spatial index of a skin feature (in this case, a benign nevus) may be computed from the surrounding vertices by expanding a radius from a feature reference point (302) until the expanding circle encompasses three points (304) that contain the feature reference (302); the numerical value of the point 302 is an interpolation of the values of the three vertices (304). Other interpolation methods exist.

Figure 4A:
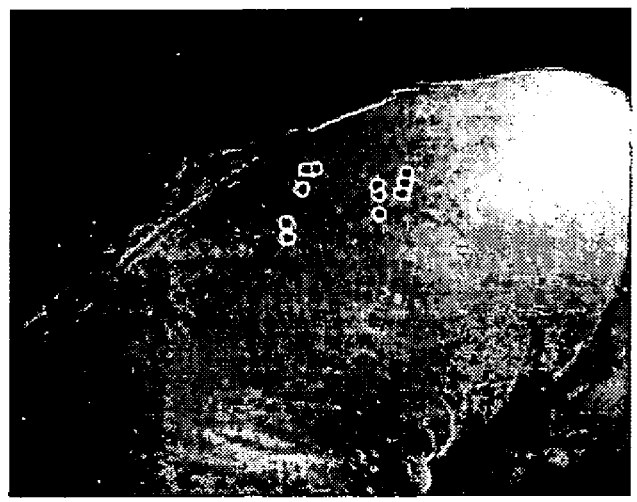
FIGS. 4A-B are exemplary images of the dorsal surface of a thumb that have the points of emersion of corresponding hair shafts from the stratum corneum labeled, to enable the matching and registration of surface features.
Figure 4B:
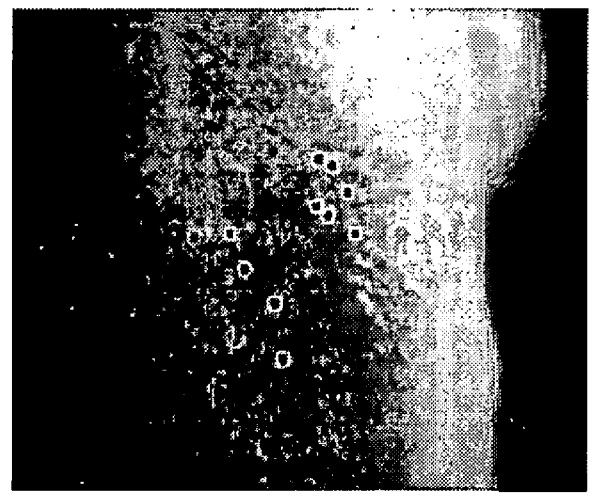

FIGS. 4A-B are exemplary images of the dorsal surface of a thumb that have the points of emersion of corresponding hair shafts from the stratum corneum labeled, to enable the matching and registration of surface features, such as detecting changes in pigmented lesions that might be associated with melanoma. These figures demonstrate that a feature may adopt a global coordinate system as well as local labeling information. In this case the points of emersion of hair shafts provide local labeling information that may be used for managing the imaging data. The ability to identify points of correspondence at such a fine scale that also possess stability over time allows surface features to be better matched from one observation to the next since differences in the local deformation of the skin may be compensated for. The local labeling information provided by the points of emersion of the hair shafts provide a much finer level of detail than that provided by geometric (height, width, etc.) and those provided by cardinal reference points, and which may be needed for certain imaging data that require such a fine labeling.

An alternative system and method for managing imaging data using a 3D surface mesh uses a more simplified setup using images obtained by a video camera, which is more readily available and affordable than some of the more sophisticated system, such as those described above. For example, in the application of lesion indexing, a video survey of the body surface (panning a video camera over the skin to capture it in a series of strips) replaces the construction of a whole 3D body model. In this scenario, the video streams is edited into a series of segments accessible through a table of contents (e.g., similar to the scene selection mode on a movie DVD) and 3D models need only be constructed for local regions of clinical interest. In one way this alternative method allows higher resolution images or 3D models to be opened making the selection of surface detail easier, more accurate, or even, in some cases, possible. Using the video-based approach, the techniques also includes methods to link information (e.g., high resolution images, clinical notes, other patient data) to specific portions of the video stream by providing a table of the frames associated with each feature and by counting the displayed frames so that an event (e.g., mouse click, key press, voice command) can use the current count together with the table data to retrieve the supplementary information. A way to accomplish at least part of the functionality of being able to use an action (e.g., a mouse click) to retrieve additional information could be accomplished by implementing a method to number frames and then to count them as they are displayed. Supplemental information could be matched to a range of frames. When a mouse click, key press, or voice command occurs, any information associated with the current frame number halts the movie and replaces it in the window, or alternatively, allows the movie to continue and opens a new window(s) or inset(s).

REFERENCES

The following references are examples of the various techniques that are available or which may be adapted for the purposes of the embodiments of the present invention. For example, see Brett Allen, Brian Curless and Zoran Popovic (2003) The space of human body shapes: reconstruction and parameterization from range scans. ACM Transactions on Graphics, 22(3):587-594, for available technique to change body shapes by manipulating parameters. Also, see H. Seo, F. Cordier, and N. Magnenat-Thalmann (2003) Synthesizing Animatable Body Models with Parameterized Shape Modifications. ACM SIGGRAPH Eurographics Symposium on Computer Animation, pp. 120-125, for another available technique to change body shapes by manipulating parameters.

For techniques to change pose of skin surface by articulating a skeleton, see for example, Brett Allen, Brian Curless and Zoran Popovic (2002) Articulated body deformation from range scan data. ACM Transactions on Graphics, 22(3):612-619, and J. F. Oliveira, D. Zhang, B. Spanlang and B. Buxton (2003) Animating scanned human models. WSCG'2003, Plzen, Czech Republic.

For techniques to simplify a 3D mesh, see for example, Vijay Natarajan and Herbert Edelsbrunner (2004) Simplification of three-dimensional density maps. IEEE Transactions on Visualization and Computer Graphics, (in press).

For techniques to reduce mesh density, see for example, P. Alliez and M. Desbrun (2001) Progressive compression for lossless transmission of triangle meshes. Proceedings of SIGGRAPH, Los Angeles, Calif., pp. 195-202.

For techniques to adjust 3D body models by deformation, see for example, Xiangyang Ju and J. Paul Siebert (2001) Individualising Human Animation Models, Proc. Eurographics 2001, Manchester, UK; and W. Lee and N. Magnenat-Thalmann (2001) Virtual Body Morphing. Proc. Computer Animation, Seoul, Korea.

For techniques to use anatomical landmarks to anchor a 3D mesh, see for example, M. Bock, A. Bowman, and P. Siebert, (2002) Data extraction from dense 3D surface models. Compstat 2002, Proc. 15th Int. Conf. on Computational Statistics, August 24-28, Bremen, Germany.

For one technique to pose patients in a standardized position, see for example, A. C. Halpern, A. A. Marghoob, T. W. Bialoglow, W. Witmer, and W. Slue (2003) Standardized positioning of patients (poses) for whole body cutaneous photography. Journal of the American Academy of Dermatology 49:593-8.

For a survey of skin imaging methods, see for example, A. A. Marghoob, L. D. Swindle, C. Z. Moricz, F. A. Sanchez Negron, B. Slue, A. C. Halpern, and A. W. Koph (2003) Instruments and new technologies for the in vivo diagnosis of melanoma. Journal of the American Academy of Dermatology, 49:777-97.

For a demonstration of the utility of body imaging and dermoscopy, see for example, S. Q. Wang, A. W. Koph, K. Koenig, D. Polsky, K. Nudel, and R. S. Bart (2004) Detection of melanomas in patients followed up with total cutaneous examinations, total cutaneous photography, and dermoscopy. Journal of the American Academy of Dermatology, 50(1):15-20.

For techniques to register multiple 3D models acquired at different times, see for example, A. Johnson and M. Herbert (1997) Surface Registration by Matching Oriented Points. International Conference on Recent Advances in 3-D Digital Imaging and Modeling, pp. 121-128; B. McGregor (1998) Automatic registration of images of pigmented skin lesions. Pattern Recognition, 31(6):805-817; and D. Chetverikov, D. Svirko, D. Stepanov and P. Kresk (2002) The trimmed iterative closest point algorithm. ICPR02, pp. 545-548.

For techniques to make a 3D model from multiple views, see for example, Daniel F. Huber (2002) Automatic three-dimensional modeling from reality. Robotics Institute, Carnegie Mellon University, CMU-RI-TR-02-35.

For techniques to imbed hyperlinks in video, see for example, Jason McC. Smith and David Stotts (2002) An extensible object tracking architecture for hyperlinking in real-time and stored video streams. Department of Computer Science, University of North Carolina, TR02-017.

For techniques for making 3D models from video, see for example, P. M. Q. Aguiar and J. M. F. Moura (2001) Three-dimensional modeling from two-dimensional video. IEEE Transactions on Image Processing, 10(10):1541-1551; and Marc Pollefeys, Luc Van Gool, Maarten Vergauwen, Frank Verbiest, Kurt Cornelis and Jan Tops (2002) Video-to-3D. PCV02 Photogrammetric Computer Vision ISPRS Commission III, Symposium 2002, Sep. 9-13, 2002, Graz, Austria, p. A-252-257.

For techniques for associating specified program actions with locations in images viewed on a computer system, see for example, U.S. Pat. No. 6,616,701, Method and apparatus for identifying features of multidimensional image data in hypermedia systems.

As will be understood by those of skill in the art, the embodiments of the present invention may be practiced in other specific forms without departing from the essential characteristics thereof. For example, any number of available transforms may be used to generate a three-dimensional representation of a body of a subject from a series of two-dimensional images, or any number of techniques may be used to generate a 3D surface mesh. Accordingly, the foregoing is intended to be illustrative, but not limiting of the scope of the invention, which is set forth in the following claims.

What is claimed is:

1. A method of managing imaging data related to a biological trait, comprising:
    generating a discretized three-dimensional mathematical surface representation of the entire external surface of the body of a patient;
    mapping the discretized three-dimensional mathematical surface representation into a coordinate system based upon the patient's anatomical landmarks;
    obtaining an imaging data related to a biological trait;
    associating said imaging data with a coordinate location of said discretized three-dimensional mathematical surface representation, to generate an associated imaging data, wherein said associated imaging data comprises data related to a biological trait and data related to the anatomical landmark; and
    managing said associated imaging data using said discretized three-dimensional mathematical surface representation.

2. The method of claim 1 wherein said generating comprises generating a representation comprising a three-dimensional surface grid of the body of a patient.

3. The method of claim 2 wherein said generating comprises generating a surface grid comprising a variable resolution discretization.

4. The method of claim 1 wherein said generating comprises generating a representation comprising a three-dimensional representation of the epithelial surfaces accessible through the bodily surfaces of the patient.

5. The method of claim 4 wherein said epithelial surface comprises the gastrointestinal surface of the patient.

6. The method of claim 4 wherein said epithelial surface comprises the vaginal and reproductive tract.

7. The method of claim 4 wherein said epithelial surface comprises the sinus area.

8. The method of claim 4 wherein said epithelial surface comprises eye ground findings.

9. The method of claim 1 wherein said generating a discretized three-dimensional mathematical surface representation comprises generating a three-dimensional surface having a rigging, so as to enable the three-dimensional surface to be adjusted for the patient's pose.

10. The method of claim 1 wherein said generating a discretized three-dimensional mathematical surface representation comprises generating a three-dimensional surface having a geometric reference coordinate system.

11. The method of claim 1 wherein said generating a discretized three-dimensional mathematical surface representation comprises generating a three-dimensional surface having cardinal reference points to form local coordinate systems.

12. The method of claim 1 wherein said obtaining comprises obtaining an imaging data comprising dermatological data.

13. The method of claim 1 wherein said obtaining comprises obtaining an imaging data comprising external surface and subsurface structure of the body of the patient.

14. The method of claim 1 wherein said obtaining comprises obtaining an imaging data comprising dermatological data including skin markings comprising nevi, vascularities, lesions, scars or combinations thereof.

15. The method of claim 1 wherein said obtaining comprises obtaining an imaging data comprising a follicular pattern.

16. The method of claim 1 wherein said obtaining said imaging data comprises obtaining a high resolution imaging data comprising a dermatological data.

17. The method of claim 16 wherein said high resolution imaging data is a dermatological data including skin markings comprising nevi, vascularities, lesions or a follicular pattern.

18. The method of claim 16 wherein said obtaining a high resolution imaging data is obtaining an imaging data having a resolution that is sufficiently high for the purposes of a medical diagnosis, or cosmetic or forensic identification.

19. The method of claim 1 wherein said obtaining comprises obtaining a two-dimensional imaging data.

20. The method of claim 1 wherein said associating comprises mapping a two-dimensional image having a surface landmark onto a three-dimensional representation, wherein said landmark is retained in said three-dimensional representation and wherein said landmark is used for said managing.

21. The method of claim 20 wherein said two-dimensional image is obtained using a camera and wherein said two-dimensional image is one of a plurality of two-dimensional images, taken with a camera or cameras at different camera positions, wherein each of said images includes a surface landmark, and wherein said three-dimensional representation accommodates said different camera positions to maintain a relationship between the two-dimensional image, its three-dimensional mapped version and its landmark.

22. The method of claim 21 wherein said three-dimensional representation of said two-dimensional image is maintained at a different resolution than said two-dimensional image, and wherein said three-dimensional representation maintains information related to the resolution of said two-dimensional image before said two-dimensional image was mapped to said three-dimensional representation.

23. The method of claim 1 wherein said associating comprises mapping said imaging data to a portion of said surface representation, wherein said portion includes said coordinate location.

24. The method of claim 1 wherein said managing is labeling, indexing, cataloging, accessing, retrieving, displaying, monitoring or comparing said associated imaging data.

25. The method of claim 24 wherein said comparing comprises registering multiple sets of said associated imaging data using a three-dimensional matching algorithm.

26. The method of claim 1 wherein said imaging data comprises data used for the identification of an individual and said managing comprises an indexing for said identification.

27. The method of claim 1 wherein said biological data comprises dermatological data and said landmark data comprises hair follicle data.

28. A method of managing imaging data related to a biological trait, comprising:
    generating a discretized three-dimensional mathematical surface representation of the entire external surface of the body of a patient, wherein said generating a discretized three-dimensional mathematical surface representation comprises generating a three-dimensional surface having a rigging, so as to enable the three-dimensional surface to be adjusted for the patient's pose;

mapping the discretized three-dimensional mathematical surface representation into a coordinate system based upon the patient's anatomical landmarks;

obtaining an imaging data related to a biological trait, wherein said obtaining comprises obtaining a high resolution imaging data comprising dermatological data including skin markings comprising nevi, vascularities, lesions, scars or combinations thereof;

associating said imaging data with a coordinate location of said discretized three-dimensional mathematical surface representation, to generate an associated imaging data, wherein said associating comprises mapping a two-dimensional image having a surface landmark onto a portion of the three-dimensional representation, wherein said portion includes said coordinate location and wherein said landmark is retained in said three-dimensional representation and wherein said landmark is used for said managing; and managing said associated imaging data using said discretized three-dimensional mathematical surface representation, wherein said imaging data is a two-dimensional image and is obtained using a camera and wherein said two-dimensional image is one of a plurality of two-dimensional images, taken with a camera or cameras at different camera positions, wherein each of said images includes a surface landmark, and wherein said three-dimensional representation accommodates said different camera positions to maintain a relationship between the two-dimensional image, its three-dimensional mapped version and its landmark.

29. A system for managing imaging data related to a biological trait, comprising:

means for generating a discretized three-dimensional mathematical surface representation of the entire external surface of the body of a patient;

means for mapping the discretized three-dimensional mathematical surface representation into a coordinate system based upon the patient's anatomical landmarks;

means for obtaining an imaging data related to a biological trait;

means for associating said imaging data with a coordinate location of said discretized three-dimensional mathematical surface representation, to generate an associated imaging data, wherein said associated imaging data comprises data related to a biological trait and data related to the anatomical landmark; and means for managing said associated imaging data using said discretized thee-dimensional mathematical surface representation.

30. The system of claim 29 wherein said discretized three-dimensional mathematical surface representation comprises a three-dimensional surface grid of the body of a patient.

31. The system of claim 30 wherein said discretized three-dimensional mathematical surface representation comprises a surface grid comprising a variable resolution discretization.

32. The system of claim 29 wherein said discretized three-dimensional mathematical surface representation comprises a representation comprising a three-dimensional representation of the epithelial surfaces accessible through the bodily surfaces of the patient.

33. The system of claim 32 wherein said epithelial surface comprises the gastrointestinal surface of the patient.

34. The system of claim 32 wherein said epithelial surface comprises vaginal and reproductive tract.

35. The system of claim 32 wherein said epithelial surface comprises the sinus area.

36. The system of claim 32 wherein said epithelial surface comprises eye ground findings.

37. The system of claim 29 wherein said means for generating a discretized three-dimensional mathematical surface representation generates a three-dimensional surface having a rigging, so as to enable the three-dimensional surface to be adjusted for the patient's pose.

38. The system of claim 29 wherein said means for generating a discretized three-dimensional mathematical surface representation generates a three-dimensional surface having a geometric reference coordinate system.

39. The system of claim 29 wherein said means for generating a discretized three-dimensional mathematical surface representation generates a three-dimensional surface having cardinal reference points to form local coordinate systems.

40. The system of claim 29 wherein said imaging data comprises an imaging data comprising dermatological data.

41. The system of claim 29 wherein said imaging data comprises imaging data comprising external surface and subsurface structure of the body of the patient.

42. The system of claim 29 wherein said imaging data comprises imaging data comprising dermatological data including skin markings comprising nevi, vascularities or lesions.

43. The system of claim 29 wherein said imaging data comprises imaging data comprising a follicular pattern.

44. The system of claim 29 wherein said imaging data comprises a high resolution imaging data comprising a dermatological data.

45. The system of claim 44 wherein said high resolution imaging data is a dermatological data including skin markings comprising nevi, vascularities, lesions or a follicular patter.

46. The system of claim 44 wherein said high resolution imaging data is an imaging data having a resolution that is sufficiently high for the purposes of a medical diagnosis, or cosmetic or forensic identification.

47. The system of claim 29 wherein said imaging data is a two-dimensional imaging data.

48. The system of claim 29 wherein said means for associating comprises routines for mapping a two-dimensional image having a surface landmark onto a three-dimensional representation, wherein said landmark is retained in said three-dimensional representation and wherein said landmark is used for said managing.

49. The system of claim 48 wherein said two-dimensional image is one of a plurality of two-dimensional images, taken with a camera or cameras at different camera positions, wherein each of said images includes a surface landmark, and wherein said three-dimensional representation accommodates said different camera positions to maintain a relationship between the two-dimensional image, its three-dimensional mapped version and its landmark.

50. The system of claim 48 wherein said three-dimensional representation of said two-dimensional image is maintained at a different resolution than said two-dimensional image, and wherein said three-dimensional representation maintains information related to the resolution of said two-dimensional image before said two-dimensional image was mapped to said three-dimensional representation.

51. The system of claim 29 wherein said means for associating comprises routines for mapping said imaging data to a portion of said surface representation, wherein said portion includes said coordinate location.

52. The system of claim 29 wherein said means for managing comprises a routine for labeling, indexing, cataloging, accessing, retrieving, displaying, monitoring or comparing said associated imaging data.

53. The system of claim 29 wherein said imaging data comprises data used for the identification of an individual and said means for managing comprises a routine for an indexing for said identification.

54. A system for managing imaging data related to a biological trait, comprising:
   means for generating a discretized three-dimensional mathematical surface representation of the entire external surface of the body of a patient, wherein said generating a discretized three-dimensional mathematical surface representation comprises generating a three-dimensional surface having a rigging, so as to enable the three-dimensional surface to be adjusted for the patient's pose;
   means for mapping the discretized three-dimensional mathematical surface representation into a coordinate system based upon the patient's anatomical landmarks;
   means for obtaining an imaging data related to a biological trait, wherein said obtaining comprises obtaining a high resolution imaging data comprising dermatological data including skin markings comprising nevi, vascularities, lesions, scars or combinations thereof;
   means for associating said imaging data with a coordinate location of said discretized three-dimensional mathematical surface representation, to generate an associated imaging data, wherein said associating comprises mapping a two-dimensional image having a surface landmark onto a portion of the three-dimensional representation, wherein said portion includes said coordinate location and wherein said landmark is retained in said three-dimensional representation and wherein said landmark is used for said managing; and
   means for managing said associated imaging data using said discretized three-dimensional mathematical surface representation,
   wherein said imaging data is a two-dimensional image and is obtained using a camera and wherein said two-dimensional image is one of a plurality of two-dimensional images, taken with a camera or cameras at different camera positions, wherein each of said images includes a surface landmark, and wherein said three-dimensional representation accommodates said different camera, positions to maintain a relationship between the two-dimensional image, its three-dimensional mapped version and its landmark.

* * * * *